United States Patent
Emmrich et al.

(10) Patent No.: US 9,700,041 B2
(45) Date of Patent: Jul. 11, 2017

(54) WEARABLE INSECT REPELLING PATCH

(71) Applicant: S.C. Johnson & Son, Inc., Racine, WI (US)

(72) Inventors: Robert R. Emmrich, Racine, WI (US); Phillip Kongshaug, Racine, WI (US); Esther M. Helding, Racine, WI (US); Daniel T. Ropiak, Kenosha, WI (US)

(73) Assignee: S. C. Johnson & Son, Inc., Racine, WI (US)

( * ) Notice: Subject to any disclaimer, the term of this patent is extended or adjusted under 35 U.S.C. 154(b) by 0 days.

(21) Appl. No.: 14/721,431

(22) Filed: May 26, 2015

(65) Prior Publication Data

US 2015/0320039 A1    Nov. 12, 2015

Related U.S. Application Data

(63) Continuation of application No. 11/359,089, filed on Feb. 22, 2006, now abandoned.

(60) Provisional application No. 60/655,998, filed on Feb. 24, 2005.

(51) Int. Cl.
*A01N 53/00* (2006.01)
*A01N 57/12* (2006.01)
*A01N 25/34* (2006.01)
*A01N 25/10* (2006.01)
*A41D 13/00* (2006.01)

(52) U.S. Cl.
CPC .............. *A01N 25/10* (2013.01); *A01N 25/34* (2013.01); *A01N 53/00* (2013.01); *A41D 13/001* (2013.01); *Y10T 442/2525* (2015.04)

(58) Field of Classification Search
CPC ........ A01N 53/00; A01N 57/12; A01N 25/10; A01N 25/34; A01N 2300/00; A41D 13/001; Y10T 442/2525
See application file for complete search history.

(56) References Cited

PUBLICATIONS

Rozendaal (Vector Control, 1997, WHO pp. 59-63, 86-91; 14 pages total).*

\* cited by examiner

*Primary Examiner* — Ernst V Arnold

(57) ABSTRACT

An insect repellent patch is disclosed of a size and weight compatible for wearing on the clothing or skin of a user. The patch has a gross area not in excess of 232 cm$^2$ and bearing one or more insect repellents having a vapor pressure at 25° C. of not less than about $1 \times 10^{-6}$ mm Hg. The total amount of insect repellent is in an amount effective to provide practical mosquito personal area repellency. Kits of such patches, with instructions for use, and methods of providing practical personal area insect repellency are also disclosed.

17 Claims, 3 Drawing Sheets

WEARABLE INSECT REPELLING PATCH

CROSS-REFERENCE TO RELATED APPLICATIONS

This application is a continuation of U.S. patent application Ser. No. 11/359,089 filed Feb. 22, 2006 which claims priority on U.S. Provisional Patent Application No. 60/655,998, filed Feb. 24, 2005.

STATEMENT REGARDING FEDERALLY SPONSORED RESEARCH/DEVELOPMENT

Not applicable

BACKGROUND OF THE INVENTION

The invention relates to the field of insect repellents and specifically to personal area repellents.

Personal insect repellents, such as DEET-containing lotions and sprays, are commonly applied directly to the skin of a user. DEET and certain other active ingredients are recognized in the art as efficacious when so used. However, these personal insect repellents, while they may discourage mosquitoes from landing on treated surfaces, typically do not actually repel the mosquitoes from the area, even from the area directly surrounding a user. Furthermore, to be effective, a user's exposed skin must be directly treated, and some users find such a treatment to be aesthetically unsatisfactory.

The art is also generally aware of treated wrist bands, patches and other treated materials to be worn or otherwise applied to a user's skin or clothing to repel mosquitoes. These have commonly employed citronella as a repellent and purport not just to keep mosquitoes from landing on treated skin but actually to repel mosquitoes from the area immediately surrounding a wearer, thus seeking to prevent bites without the need for applying a lotion or spray to the skin.

For example, U.S. Pat. No. 5,656,282 teaches the use of patches attachable to clothing or limbs that disperse citronella. This patent also describes using adhesives and hook and loop type materials for attachment purposes, and describes that the pouch could alternatively be in the form of a band worn by the user. Also, it describes an impregnated substrate which is a nonwoven thermoplastic. However, these devices have not proved to be practically effective to protect a user wearing them from close approach by mosquitoes and other insects.

Use of transfluthrin, vaporthrin, and/or DDVP to control insects via passive evaporation (without requiring heating of a substrate or blowing air) is known in the context of room insect control. See e.g. U.S. Pat. No. 6,582,714. See also U.S. Pat. No. 6,534,079 which describes use of, among other things, transfluthrin for passive room insect control.

Having metofluthrin or profluthrin passively evaporate and control insects for room control is known from U.S. patent application publication 2004/0134999.

The art is also aware of commercially available, repellent/insecticide-treated clothing and bed nets. For example, U.S. Pat. No. 6,896,892 describes impregnating clothing with varied repellents, albeit in a slow release repellent mix. However, the repellents used in such devices are often not effective in keeping insects away from a consumer (as opposed to minimizing landing time).

The art is also aware of wearable devices for achieving personal area repellency, using treated substrates subjected to heat and/or air moved by a fan or similar means over or through a treated substrate. These devices can be efficacious, although they require an energy source and inevitably have a size and bulk that a user must be willing to tolerate.

Hence, the art has not yet optimized means of providing repellency protection to a consumer, particularly with respect to avoiding use of energy consuming devices, bulky devices, or large devices.

BRIEF SUMMARY OF THE INVENTION

In a first aspect of the invention there is an insect repellent patch having a delivery substrate no greater than 232 cm$^2$ in gross area, bearing insect repellent having a vapor pressure at 25° C. of not less than $1 \times 10^{-6}$ mm Hg. The insect repellent is present in a total amount effective to provide practical mosquito personal area repellency. In preferred forms the insect repellent patch bears not less than a total of 0.17 mg/cm$^2$ of such insect repellent. The patches may be stick-on patches, or may be in the form of wrist, ankle, arm or leg bands, or may be in the form of pendants or medallions.

For example, the delivery substrate may have a front side and a back side, and a fastener linked to the substrate that is capable of releasably attaching the patch to a supporting surface selected from the group consisting of a user's skin and/or clothing, and wherein the fastener is selected from the group consisting of adhesives, pins, hook-and-eye fastener material, a frame, and/or a band.

In especially preferred forms the patch is suitable to dispense at least 0.01 mg of insect repellent per hour at 25° C. in still air conditions, the insect repellent is a pyrethroid insect repellent selected from the group consisting of transfluthrin, metofluthrin, and profluthrin, the patch has a substrate bearing the repellent, the substrate being formed from a material selected from the group consisting of polypropylene, polyethylene, polyester, nylon, rayon, cellulose acetate, wood pulp and cotton. Particularly preferred plastic materials are non-woven fabrics which are spunbonded, spunlaced, spunlaid, melt blown, needle punched, hydroentangled, latex bonded, and/or resin bonded.

Interestingly, we have learned that protection is enhanced when a patch is formed by dosing the substrate with a mix of a dose of solvent and an amount of said insect repellent, the solvent is allowed to evaporate off from the substrate, and, preferably, the substrate is pre-exposed to ambient atmospheric conditions for at least 1 hour prior to using the patch for personal area insect repellency protection or to containing the patch in an insect repellent-tight envelope. The enhancement is as compared to using such a structure when the pre-evaporation step and/or the pre-exposure step has not occurred prior to beginning use.

In another form the invention provides a kit for controlling insects. The kit has at least two insect repellent patches as well as instructions to place the patches on or adjacent a user's body. These patches have a delivery substrate no greater than 232 cm$^2$ in gross area, and bear insect repellent having a vapor pressure at 25° C. of not less than $1 \times 10^{-6}$ mm Hg.

In yet another form the invention provides method of repelling mosquitoes from an immediate area around a user's body. One releasably attaches to one or both of a user's skin or clothing at least one insect repellent patch comprising a delivery substrate no greater than 232 cm$^2$ in gross area, the attached patch or patches bearing insect repellent having a vapor pressure at 25° C. of not less than $1\times10^{-6}$ mm Hg. The total amount of said insect repellent so applied is an amount effective to provide practical mosquito personal area repellency.

The patches can be placed at a variety of locations such as around wrists or ankles, near the shoulders or chest, along the calves or lower limbs, or on clothing adjacent to these positions. Most preferably multiple such patches are used, with one such patch above the waist and one below.

In still another form there is provided an insect repellent patch with a delivery substrate no greater than 232 cm$^2$ in gross area, bearing a qualifying insect repellent (as that term is defined below) in an amount effective to provide practical mosquito personal area repellency. For example the patch can be a multi-layer structure with an upper impregnated non-woven fiber material layer, an adhesive layer, and a peel-off layer.

When the patch is in the form of a stick-on patch, an adhesive layer can form the fastener.

When the patch is in the form of an ankle or wrist band, an appropriate band structure can be glued, sewed or otherwise fastened to opposed ends of the patch, with the outer ends of the band structure bearing hook and loop type fastener or other means to hold the band in place.

When the patch is in the form of a medallion, the fastener may be in the form of a frame, where the frame has a suitable fastener to link to a user's clothing (e.g. a pin structure).

When the patch is in the form of a pendant, the fastener could be in the form of a necklace string or chain attached at opposite ends to the patch.

It should be appreciated that the present invention therefore provides very small and lightweight patch structures that can readily be positioned adjacent a person to be protected. These are constructed to efficiently dispense actives to protect the area immediately surrounding the consumer.

The patches are of a type that can be readily and inexpensively manufactured. Further, they are of a size and weight that a consumer would tolerate wearing.

The foregoing and other advantages of the present invention will be apparent from the following description. In the description reference is made to the accompanying drawings which form a part thereof, and in which there is shown by way of illustration, and not limitation, preferred embodiments of the invention. Such embodiments do not necessarily represent the full scope of the invention, and reference should therefore be made to the claims herein for interpreting the scope of the invention.

DETAILED DESCRIPTION OF THE PREFERRED EMBODIMENTS

A. Definitions

In connection with this application the following definitions will be helpful:

(a) "Gross area" is defined as being the overall top and bottom plan view area of the patch, such as can be measured with a ruler or similar device, as opposed to the "surface area", which latter term includes the surfaces contained within the gross area that result from undulations in the substrate, porosity, and the like, but excludes area from which repellent cannot be dispensed (e.g. due to being covered by a barrier layer). Unless expressly stated to the contrary, patch areas described herein are gross areas.

(b) "Practical mosquito personal area repellency" is defined as at least a 70% reduction of mosquitoes from the immediate area around a user's body.

(c) "The immediate area around a user's body" is defined as an area within 1 meter of a person's body.

(d) "Effective amount" of a insect repellent or other active material is defined as that amount that is sufficient to provide the indicated result within 20 minutes in a substantially wind-free location.

(e) A "qualifying insect repellent" is defined as a repellent that provides practical mosquito personal area repellency of not less than 70% as compared to controls within 20 minutes when two patches 103 cm$^2$ in size are tested in the apparatus and by the method described in Example 1, below, each patch treated with 60 mg of the repellent and each patch not having an adhesive layer on either side.

B. Preferred Insect Repellent Actives

Certain insect repellent active ingredients having the desired vapor pressure characteristics that will be referred to herein are identified in the following table:

| ISO Common Name | Trade Name | Chemical Name | CAS # | Vapor pressure |
|---|---|---|---|---|
| Metofluthrin | | 2,3,5,6-tetrafluoro-4-methoxymethylbenzyl (EZ)-(1RS,3RS)-2,2-dimethyl-3-(prop-1-enyl)-cyclopropanecarboxylate | 240494-70-6 | $3.4 \times 10^{-6}$ mm Hg @ 25° C. |
| Profluthrin | | 2,3,5,6-tetrafluoro-4-methylbenzyl (EZ)-(1RS,3RS)-2,2-dimethyl-3-(prop-1-enyl)-cyclopropanecarboxylate | n/a | $7.73 \times 10^{-5}$ mm Hg @ 25° C. |
| Transfluthrin | Bayothrin | (1R-trans)-(2,3,5,6-tetrafluorophenyl)-methyl-3-(2,2- | 118712-89-3 | $3.0 \times 10^{-6}$ mm Hg @ |

| ISO Common Name | Trade Name | Chemical Name | CAS # | Vapor pressure |
|---|---|---|---|---|
| | | dichloroethenyl)-2,2-dimethylcyclopropanecarboxylate | | 20° C. |
| Emphenthrin | Vaporthrin | (RS)-1-ethynyl-2-methyl-2-pentenyl-(1RS,3RS)-2,2-dimethyl-3-(2-methylpropenyl)-cyclopropanecarboxylate | 54406-48-3 | $6.5 \times 10^{-4}$ mm Hg @ 20° C. |
| Diclorvos | DDVP | 2,2-dichlorovinyl dimethyl phosphate | 62-73-7 | $1.2 \times 10^{-5}$ mm Hg @ 20° C. |

C. Preferred Embodiments

Figure 1:
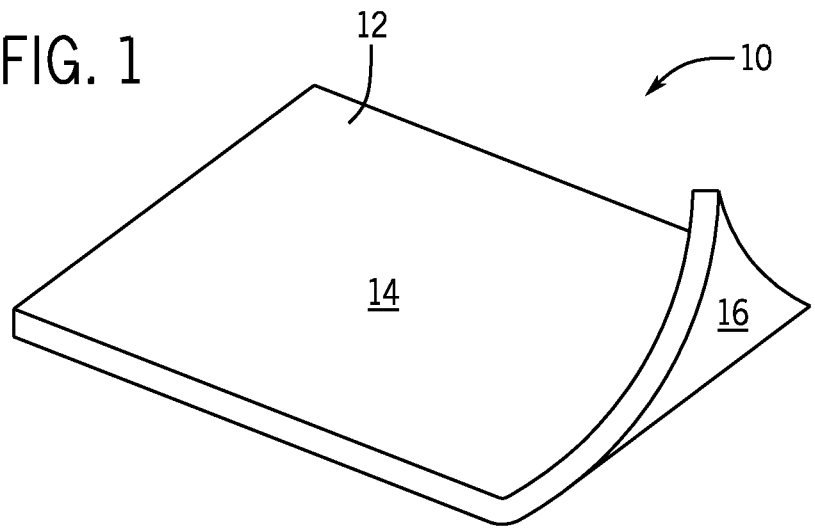
FIG. 1 is a perspective view of an insect repellent patch according to one preferred embodiment of the invention, with one corner turned up to reveal a portion of its back side.

Turning first to FIG. 1, an insect repellent patch made in accord with the invention is shown generally at 10. The patch 10 has a delivery substrate 12 having a front side 14 and a back side 16. At least one of the front and back sides 14,16 are exposed to the surrounding air when the patch 10 is in use (typically the front side). The size of the patch 10 must be small enough that a user can wear one or more patches without inconvenience, and thus the patch of the invention is restricted to a size not greater than about 232 cm².

Figure 2:
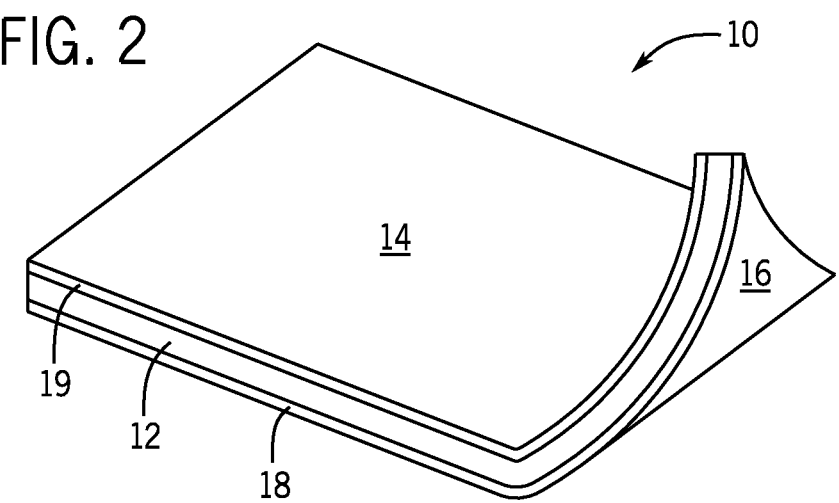
FIG. 2 is a perspective view similar to that of FIG. 1, but of an alternative embodiment.

The patch 10 in the embodiment shown in FIG. 2 also includes an adhesive 18 for attaching the patch 10 to a supporting surface (not shown). Any fastener device or material capable of attaching the patch 10 to the desired supporting surface can be substituted for the adhesive 18. Non-limiting examples of such alternative fasteners include pins (such as conventional safety pins, for example), spring clips, hook-and-eye fastener materials (such as those sold under the Velcro® brand name, for example), a frame attachable to a user or a user's clothing and capable of holding a patch 10, and the like.

Also, the lateral ends of the patch can be instead linked to band material for a wrist band or ankle band structure, or for a pendant chain, where the ends of the band material or chain material link together to form a loop. See for example the band segments partially illustrated at 38 in FIG. 4.

When used, the adhesive 18 can be conveniently located on the back side 16, although framing or alternative, equivalent locations for adhesive will be apparent to one skilled in the art. When the patch 10 is worn by a user, the adhesive 18 or alternative fastener must be capable of attaching the patch to the user's skin and/or clothing. In any event, it is advantageous that the adhesive 18 or alternative fastener be capable of releasably attaching the patch to the supporting surface, allowing the patch 10 to be conveniently applied and removed, as desired.

The delivery substrate 12 may be made of any generally non-porous, lipophilic material, such as woven or felted rayon, polyester, polypropylene, polyethylene, nylon, or the like. The delivery substrate 12 is dosed with an insect repellent having a vapor pressure at 25° C. of not less than about $1 \times 10^{-6}$ mmHg. Non-limiting examples of insect repellents that are suitable include the following: transfluthrin, metofluthrin, profluthrin, and diclorvos.

The selected insect repellent, or mixture of such repellents, is applied to the delivery substrate 12 in an amount effective to provide practical mosquito personal area repellency. When multiple patches 10 are to be used in concert, that amount must be such that at least the total amount of insect repellent applied to the delivery substrates 12 of the patches is, collectively, an amount effective to provide practical mosquito personal area repellency.

Such insect repellents can be dissolved in acetone or a similar, easily evaporated solvent. The solution can then be applied to the delivery substrate 12 by pipetting or any convenient way to deliver a controlled quantity of liquid. The solvent quickly evaporates, leaving the insect repellent behind, borne on the delivery substrate 12.

We have discovered that when using this form of dosing, it is particularly desirable to allow the solvent to essentially entirely evaporate off before beginning insect repellency use of the patch. Thus, it is very desirable to select a solvent which much more readily evaporates off than the repellent does, as well as evaporation conditions to achieve this.

For example, after we have dosed our substrate (e.g. a 10.2 cm×10.2 cm patch with 60 mg of transfluthrin in 2.53 ml of acetone), we place the dosed substrate in a ventilated area at 21-24° C. for 15-20 minutes. We then packaged the patch in a hermetically sealed pouch until use.

It is advantageous to post the patches about the body of the user at multiple spaced locations, thus making the simultaneous use of multiple patches 10. To facilitate that use, it is convenient to supply the patches 10, as described above, in kits containing multiple patches. In addition the kits may include instructions for their use to achieve practical mosquito personal area repellency. Consequently, kits preferably including such instructions together with two, four, or, in any event, more than one, patch are useful, with the patches contained within sealed pouches or the like (not shown), to prevent premature loss of the repellent prior to use. Alternatively, a vapor-containing seal 19 can be laminated over the delivery substrate 12 to prevent the loss of insect repellent before the seal is removed for use.

Instructions for use include instructions as to where on the body to place patches, for example, instructions to use the fastener provided to place at least one patch low on the body (for example, on a leg, calf, ankle, or foot), and at least one patch higher on the body but below the neck (for example on the chest, back, shoulder, or an arm).

The method of repelling mosquitoes from the immediate area around a user's body includes attaching to one or both of the user's skin or clothing at least one patch 10, as described above. Improved distribution of the insect repellent is achieved by attaching two or more patches 10 at locations distributed about the body. Thus, it is advantageous to locate at least one, two, or more patches 10 low on the body, for example on the leg, ankle, and/or foot, and at least one, two, or more patches above the waist but below the neck, for example on the chest, back, shoulder, and/or either or both arms.

Example 1

Figure 3:
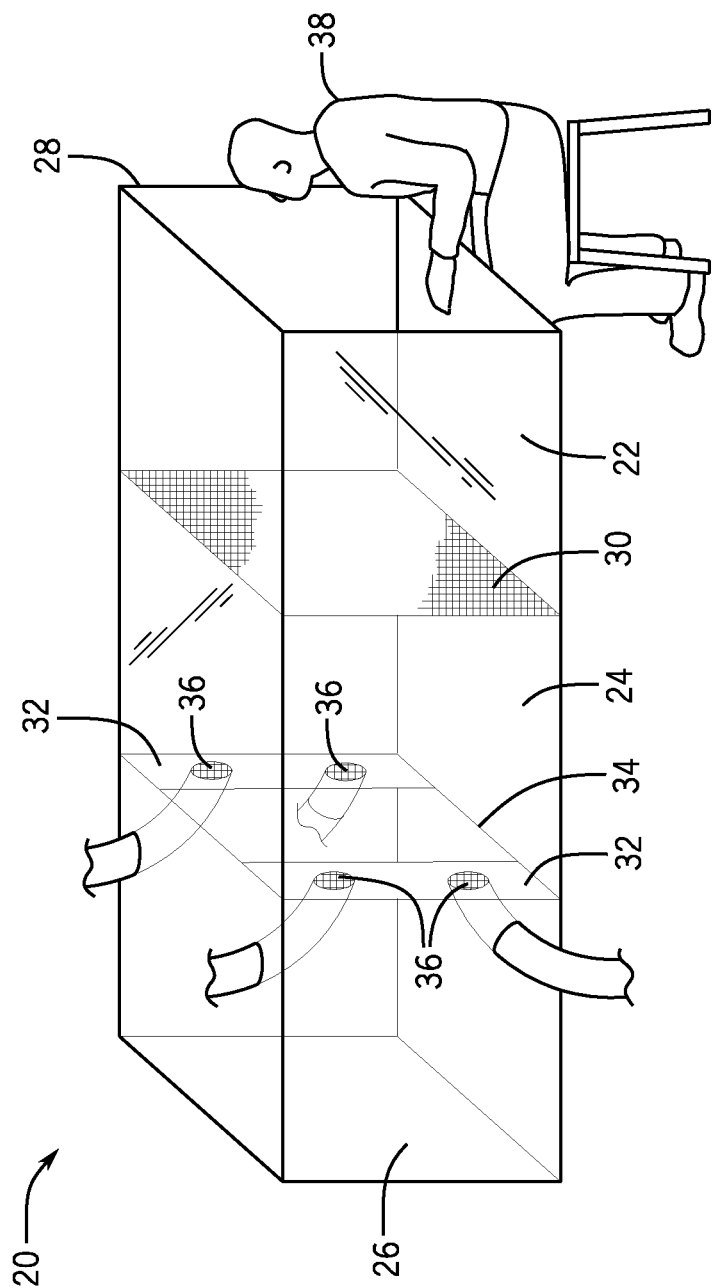
FIG. 3 is a schematic representation of one test apparatus that was used for testing insect repelling effects of insect repelling patches of the present invention.

Various patch sizes and insect repellents were tested, initially using the test apparatus shown schematically generally at 20 in FIG. 3. The test apparatus 20 has a sample chamber 22, connected to a mosquito chamber 24, which is connected via an opening 34 to a remote chamber 26. Each chamber is generally cubical, with a volume of about 0.43 $m^3$.

The sample chamber 22 has an open end 28 on the side remote from the mosquito chamber 24. A screen 30 divides the sample chamber 22 from the mosquito chamber 24. The opening 34 between the mosquito chamber 24 and the remote chamber 26 is slightly constricted by side walls 32. However, the opening 34 is still sufficiently large that mosquitoes can freely move between the mosquito and remote chambers 24 and 26.

Four, screened, low-flow exhaust ports 36 are located in the side walls 32, the exhaust ports facing the open end 28. Air is drawn through the exhaust ports 36 and exhausted from the mosquito chamber 24 at a rate sufficient to draw air in through the open end 28 but insufficient to affect the flying of mosquitoes placed in the mosquito chamber 24 or to disturb the air in the remote chamber 26.

For each test, a human test subject 38 is placed at the open end 28 of the sample chamber 22, the test subject's breath providing the warmth, $CO_2$, and moisture known to be human attractants for mosquitoes. The exhaust ports 36 pull air, along with those attractants, though the open end 28 and on through the sample chamber 22, the screen 30, and the mosquito chamber 24. The attractants thus leave the apparatus 20 without entering the remote chamber 26.

Mosquitoes are placed in the mosquito chamber 24 and are quickly attracted to the screen 30 by the human attractants. The open end 28 is large enough to expose primarily the upper torso and head of the test subject. Two patches 10 are hung one foot into the sample chamber 22 and approximately 20 cm down from the chamber's top (except as was done otherwise in particular experiments, as is noted, below). The behavior of the mosquitoes that have been attracted to the screen 30 then reveals the practical mosquito personal area repellency capabilities of the samples.

Percent repellency was calculated as the percent of mosquitoes that had been initially introduced into the mosquito chamber 24 (most of which were attracted to the screen 30 before the patches 10 were put in place), that then were repelled from the screen when the patches were introduced. The "repellency" indicated in the table, below, for time zero reflects the mosquitoes that were not yet attracted to the screen 30 by the time the test patches 10 were introduced. Repelled mosquitoes were observed to either retreat into the remote chamber 26, land on the screened exhaust ports 36, or be knocked down within the mosquito chamber 24. The patches 10 used were 103 $cm^2$ in size, with no adhesive layer 18.

The patch material was a non-woven cloth material comprised of rayon, polyester, and polypropylene (as described in published U.S. Patent Application US20040082248), dosed with 60 mg of the active ingredient. The controls used no patches. The following results were obtained, showing successful personal area repellency for metofluthrin, transfluthrin, and profluthrin when so used:

| | % Repellency | | | | |
|---|---|---|---|---|---|
| Time (minutes) | metofluthrin (2 reps) | transfluthrin (3 reps) | profluthrin (3 reps) | Control 1 | Control 2 |
| 0 | 10 | 13 | 6 | 10 | 17 |
| 5 | 72 | 54 | 55 | 5 | 13 |
| 10 | 92 | 75 | 67 | 10 | 22 |
| 15 | 96 | 90 | 91 | 5 | 22 |
| 20 | 98 | 92 | 93 | 0 | 22 |

Example 2

The same test apparatus 20 was used in the same way as described in Example 1, with the following changes. When a test included four patches 10, two were hung as in Example 1, and two were hung about 13 cm from the bottom of the chamber to simulate patches worn on the shoulders and at the waist of a user. In one test, as indicated in the table, below, the patches 10 were attached to the test subject's chest. Each individual patch was treated with the amount of insect repellent indicated. Time is shown in minutes.

The results indicate successful personal area control for transfluthrin patches where total area of the patches used was at least 51.6 $cm^2$ (2 patches, each 25.8 $cm^2$) without an adhesive layer on either side, and for DDVP (4 patches, each 103 $cm^2$ in gross area) without an adhesive layer on either side. It will be noted that emphenthrin (vaporthrin) proved not to be an insect repellent capable of providing practical mosquito personal area repellency within 20 minutes when dosed as indicated on 2 patches of the size indicated.

| Time | transfluthrin 1 rep 4 patches* 6.45 $cm^2$ 60 mg | transfluthrin 1 rep 4 patches 6.45 $cm^2$ 120 mg | transfluthrin 2 reps 2 patches 25.8 $cm^2$ 30 mg | Transfluthrin 1 rep 2 patches 103.22 $cm^2$ (taped to test subject's chest) 60 mg | emphenthrin 1 rep 2 patches 103 $cm^2$ 60 mg | DDVP 1 rep 4 patches 103 $cm^2$ 60 mg | Control No patches |
|---|---|---|---|---|---|---|---|
| 0 | 5 | 11 | 13 | 19 | 17 | 5 | 11 |
| 5 | 26 | 21 | 41 | 33 | 33 | 11 | N/A |
| 10 | 47 | 32 | 68 | 44 | 29 | 47 | 11 |
| 15 | 47 | 42 | 74 | 52 | 29 | 95 | N/A |
| 20 | 47 | 47 | 79 | 81 | N/A | 95 | 11 |
| | *4th patch added 10 minutes into test | | | | | | |

Example 3

We also conducted some field tests of the present invention in southern Florida using patches 10 dosed with metofluthrin. Human test subjects and designated untreated control entered the test site, each test subject being separated by a minimum of 25 meters (approx. 75 feet). Shortly after all test subjects and an untreated control were set up in the test site, a 15 second 'nuisance' pre-count was taken by counting or best estimating the number of mosquitoes landing or touching the visual areas on the test suit.

Directly after the 'nuisance' count, a one-minute biting pre-count of a lower leg was taken. The pre-count began by having each subject roll up one pant leg to the knee then count the number of mosquitoes landing or biting on the exposed skin over a one minute period. Once a mosquito landed, the insect was pushed away (flicked, swatted or other) from the leg.

After the precounts were made, each test subject attached insect repellent patches 10 to predetermined areas on the test suit. The location of the patches is described below. The control test subject did not handle or attach any patches to his suit.

Mosquito land or bite counts were then made as described above for the pre-counts, with counts taken every 5 minutes for the first 20 minutes. After the 20 minute count, the test subjects and controls moved locations, walking approximately 15 meters. This was followed by their immediately taking a 15-second nuisance and one-minute biting count. Additional counts were then made at 25 and 30 minutes at that new location. After the 30 minute counts, the test subjects and controls moved location again, walking approximately 15 meters. This is followed by their immediately taking a 15-second nuisance and the one-minute biting count. An additional count was then made again at 35 minutes. The test was concluded after the 35 minute count.

The patches 10 used in the test were treated with metofluthrin, the 103 cm$^2$ patches bearing 60 mg and the 51.6 cm$^2$ patches bearing about 30 mg of metofluthrin. The patch material was selected either from a substrate made of a nylon-type material or from a non-woven cloth made of rayon, polyester, polypropylene, and polyethylene fibers. No difference in performance between the two materials was detected.

Patch sizes for the various tests are indicated in the table, below. When four, 103 cm$^2$ patch samples were used, the patches were placed on the side of each shoulder and on the outwardly facing side of each knee. For the four, 51.6 cm$^2$ patch samples, the patches were placed on the side of each shoulder and on the top of the shoe. The 103 cm$^2$ patches were too big to place on the shoe, and therefore only the 51.6 cm$^2$ patches were placed there. For the two, 51.6 cm$^2$ patch testing, one patch was placed on one shoulder and another was placed on the outwardly facing side of the opposing knee.

The Average Percent Biting Repellency was calculated using the following formula:

C1=precount of control
C2=control count at time corresponding with treatment count
T1=precount for test area
T2=test area count at designated time
The percent repellency was calculated by the following formula:

$$(1-(C1 \times T2)/(T1 \times C2)) \times 100$$

| Time (min) | Percent Biting Repellency | | | |
|---|---|---|---|---|
| | 3 patches (103 cm$^2$) 2 reps | 4 patches (103 cm$^2$) 1 rep | 2 patches (51.6 cm$^2$) 3 reps | 4 patches (103 cm$^2$) 2 reps |
| 0 | 0 | 0 | 0 | 0 |
| 5 | 75 | 85 | 42 | 96 |
| 10 | 100 | 94 | 60 | 100 |
| 15 | 100 | 100 | 90 | 100 |
| 20 | 100 | 92 | 81 | 88 |
| 21 | 16 | 85 | 13 | 33 |
| 25 | 84 | 81 | 82 | 50 |
| 30 | 84 | 100 | 81 | 73 |
| 31 | 64 | 61 | 44 | 22 |
| 35 | 100 | 94 | 73 | 96 |

These results demonstrate that metofluthrin, when used with the patch sizes, dosages, and locations described, can successfully provide personal area repellency within a very brief time, even after a user has moved to a new location.

Figure 4:
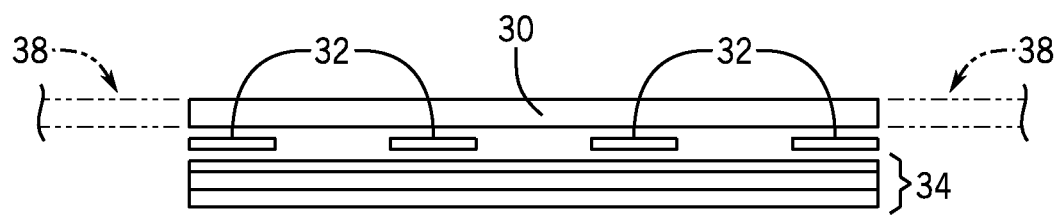
FIG. 4 is a vertical sectional view taken through a third preferred patch of the present invention.

We then tried some additional field tests with respect to mosquitoes using FIG. 4 type patches. Patches were made be adhering a multi-layer non-woven cloth made of rayon, polyester, polypropylene, and polyethylene fibers 30 to a multi-laminate foil film 34 with strips of 3M double facing tape 32. The cloth was 7.5 cm×7.5 cm in top view, and the dosing included for each patch 10 mg of metofluthrin dissolved in 2.53 ml of acetone.

We then sealed the patches in towelette pouches for storage prior to use. When the patch was to be used, we opened the pouch by tearing it open, removed the patch, peeled off the multi-laminate foil, and attached the cloth/tape structure to the specified locations.

We tested the use of two patches, the use of four patches, the use of one or two wrist bands, and the use of one or two ankle bands. All achieved over 50% repellency throughout a five minute to sixty minute monitoring under conditions of heavy mosquito populations.

We also conducted a series of experiments in which we varied the amount of time that the acetone was permitted to evaporate off prior to packaging. Interestingly, extended evaporation periods correlated for a period of days with increased performance. We would have expected just the opposite, that leaving the substrate open to evaporation might have used up the desirable active. However, at least for a period of days this effect is minimal relative to the positive effect of allowing extended evaporation periods. This is particularly odd since the acetone evaporates very quickly and very little additional acetone evaporation occurs after a day.

While the present invention has been described with reference to what are currently considered to be the preferred embodiments, it is to be understood that the invention is not limited to the disclosed embodiments. On the contrary, the invention is intended to cover various modifications and equivalent arrangements included within the spirit and scope of the appended claims. The scope of the following claims is to be accorded the broadest interpretation so as to encompass all such modifications and equivalent structures and functions.

INDUSTRIAL APPLICABILITY

The present invention provides insect repellent patches that are of a relatively small size yet can provide insect repellent control that is effective for a human.

What is claimed is:

1. An insect repellent device not linked to an energy consuming heater and not linked to a fan, the insect repellent device comprising:
a first of an insect repellent patch suitable to be worn on a user or a user's clothing; and
a second of the insect repellent patch suitable to be worn on the user or the user's clothing,
wherein the first of the insect repellent patch and the second of the insect repellent patch each comprises: (i) a delivery substrate that is 25.8 cm$^2$ to 103.22 cm$^2$ in gross area, and (ii) an insect repellent present on the substrate in a manner and in a total effective amount to provide practical mosquito personal area repellency from the first of the insect repellent patch and the second of the insect repellent patch,
wherein the substrate was formed by dosing the substrate with a mix of a dose of solvent and an amount of the insect repellent, and wherein the solvent is of a type that more readily evaporates from the substrate than the repellent does so as to leave the insect repellent behind on the substrate,
wherein the insect repellent comprises a repellent other than DEET,
wherein the insect repellent device bears not less than a total of (30 divided by 51.6) mg per cm$^2$ of exposed surface area of the insect repellent; and
wherein the insect repellent patch dispenses at least 0.01 mg of insect repellent per hour at 25° C. in still air conditions.

2. The insect repellent device of claim 1 wherein: the patch is selected from stick-on patches.

3. The insect repellent device of claim 1, wherein the delivery substrate comprises an adhesive backing.

4. The insect repellent device of claim 1, wherein the insect repellent is a pyrethroid insect repellent selected from the group consisting of transfluthrin, metofluthrin, and profluthrin.

5. The insect repellent device of claim 1, wherein the insect repellent has a vapor pressure at 25° C. of not less than 1×10$^{-6}$ mm Hg.

6. The insect repellent device of claim 1, wherein the insect repellent is present on the substrate in a manner and in a total effective amount effective to provide practical mosquito personal area repellency of not less than 80%.

7. The insect repellent device of claim 1, wherein the insect repellent is present on the substrate in a manner and in a total effective amount effective to provide practical mosquito personal area repellency of not less than 80%, and the insect repellent is transfluthrin.

8. The insect repellent device of claim 1, wherein the solvent had been permitted to evaporate from the substrate in a manner that increased the repellency of remaining insect repellent on the substrate, prior to using the device for personal area insect repellency protection, and wherein the device is capable of providing enhanced insect repellency protection after the solvent had been permitted to evaporate from the substrate as compared to an identical device in which the solvent had not been permitted to evaporate from the substrate prior to use of the device for repellency.

9. A method of repelling mosquitoes from an immediate area around a user's body, the method comprising:
releasably attaching a first of an insect repellent device on a user's skin or clothing; and
releasably attaching a second of the insect repellent device on the user's skin or clothing,
wherein the first of the insect repellent patch and the second of the insect repellent patch each comprises: (i) a delivery substrate that is 25.8 cm$^2$ to 103.22 cm$^2$ in gross area, and (ii) an insect repellent present on the substrate in a manner and in a total effective amount to provide practical mosquito personal area repellency from the first of the insect repellent device and the second of the insect repellent device,
wherein the substrate was formed by dosing the substrate with a mix of a dose of solvent and an amount of the insect repellent, and wherein the solvent is of a type that more readily evaporates from the substrate than the repellent does so as to leave the insect repellent behind on the substrate,
wherein the insect repellent comprises a repellent other than DEET,
wherein the insect repellent device bears not less than a total of (30 divided by 51.6) mg per cm$^2$ of exposed surface area of the insect repellent; and
wherein the insect repellent device dispenses at least 0.01 mg of insect repellent per hour at 25° C. in still air conditions.

10. The method of claim 9 wherein:
the insect repellent device is selected from stick-on patches, wrist bands, ankle bands, arm bands, leg bands, pendants and medallions.

11. The method of claim 9 wherein:
the insect repellent device comprises a stick-on patch.

12. The method of claim 9 wherein:
the first of the insect repellent device and the second of the insect repellent device are placed on or adjacent the user's body at two separate locations.

13. The method of claim 9 wherein:
one of the separate locations is adjacent a lower limb of the user and another of the separate locations is above the waist of the user.

14. The method of claim 9 wherein:
the first of the insect repellent device is placed on a lower limb of the user, and
the second of the insect repellent device is placed on the user's body above the waist of the user.

15. The method of claim 9 wherein:
the insect repellent is present on the substrate in a manner and in a total effective amount effective to provide practical mosquito personal area repellency of not less than 80%.

16. The method of claim 9 wherein:
the insect repellent is a pyrethroid insect repellent selected from the group consisting of transfluthrin, metofluthrin, and profluthrin.

17. The method of claim 9, wherein the solvent had been permitted to evaporate from the substrate in a manner that increased the repellency of remaining insect repellent on the substrate, prior to using the device for personal area insect repellency protection, and wherein the device is capable of providing enhanced insect repellency protection after the solvent had been permitted to evaporate from the substrate as compared to an identical device in which the solvent had not been permitted to evaporate from the substrate prior to use of the device for repellency.

* * * * *